(12) United States Patent
Kim (10) Patent No.: US 8,340,392 B2
(45) Date of Patent: Dec. 25, 2012

(54) MEDICINE PACKET INSPECTING APPARATUS

(75) Inventor: Jun-Ho Kim, Daegu (KR)

(73) Assignee: JVM Co., Ltd., Daegu (KR)

( * ) Notice: Subject to any disclaimer, the term of this patent is extended or adjusted under 35 U.S.C. 154(b) by 565 days.

(21) Appl. No.: 12/573,132

(22) Filed: Oct. 4, 2009

(65) Prior Publication Data

US 2010/0085428 A1    Apr. 8, 2010

(30) Foreign Application Priority Data

Oct. 8, 2008  (KR) .................. 10-2008-0098668

(51) Int. Cl.
*G06K 9/00* (2006.01)
(52) U.S. Cl. .................. 382/141; 348/125; 700/109
(58) Field of Classification Search .................. 382/141; 348/125; 700/109
See application file for complete search history.

(56) References Cited

U.S. PATENT DOCUMENTS

| | | | | |
|---|---|---|---|---|
| 4,190,214 A * | 2/1980 | Bond | .................... | 242/138 |
| 4,597,316 A * | 7/1986 | Ichikawa | .................... | 83/156 |
| 4,805,848 A * | 2/1989 | Birkmann et al. | ......... | 242/597.1 |
| 5,445,344 A * | 8/1995 | Seger et al. | .............. | 242/597.3 |
| 5,522,512 A * | 6/1996 | Archer et al. | .............. | 209/580 |
| 5,839,257 A * | 11/1998 | Soderstrom et al. | .......... | 53/411 |
| 6,212,855 B1 * | 4/2001 | Yasunaga et al. | .......... | 53/119 |
| 6,315,235 B1 * | 11/2001 | Breyer et al. | ............. | 242/422.4 |
| 6,330,351 B1 * | 12/2001 | Yasunaga | .............. | 382/141 |
| 6,505,461 B1 * | 1/2003 | Yasunaga | .............. | 53/562 |
| 6,804,629 B2 * | 10/2004 | Hashiguchi et al. | .......... | 702/185 |
| 7,121,397 B2 * | 10/2006 | Yuyama et al. | .............. | 193/35 R |
| 7,456,946 B2 * | 11/2008 | Ackley et al. | .............. | 356/237.1 |
| 7,954,747 B2 * | 6/2011 | Chudy et al. | .............. | 242/533.8 |
| 8,072,590 B2 * | 12/2011 | Ackley et al. | .............. | 356/237.1 |

FOREIGN PATENT DOCUMENTS

| | | |
|---|---|---|
| EP | 1 726 524 A1 | 11/2006 |
| WO | 2004/072626 A1 | 8/2004 |
| WO | 2005/017814 A1 | 2/2005 |
| WO | 2008/033019 A2 | 3/2008 |

OTHER PUBLICATIONS

European Search Report issued in European Patent App. No. EP 09172224.9 on Nov. 25, 2009.

* cited by examiner

*Primary Examiner* — Kamal Divecha
(74) *Attorney, Agent, or Firm* — Kile Park Goekjian Reed & McManus PLLC (57) ABSTRACT

A medicine packet inspecting apparatus is disclosed. The medicine packet inspecting apparatus includes a transfer conveyer installed on the upper surface of a main body to transfer medicine packets to one side of the main body, a tablet spreading unit installed on the upper surface of the transfer conveyer to uniformly spread tablets within the medicine packets, an image reading unit to capture the upper surfaces of the medicine packets with a camera and to judge whether or not the tablets are defective through comparison of the captured images with information regarding a prescription and the tablets stored in a data storage unit, and a making unit to mark a defective sign on medicine packets if the tablets within the medicine packets are judged to be defective.

4 Claims, 6 Drawing Sheets

MEDICINE PACKET INSPECTING APPARATUS

BACKGROUND OF THE INVENTION

1. Field of the Invention

The present invention relates to a medicine packet inspecting apparatus, and more particularly to a medicine packet inspecting apparatus that detects medicine packets, which are packaged differently from a prescription or contain defective tablets, such as damaged tablets.

2. Description of the Related Art

In general, a medicine packet inspecting apparatus refers to an apparatus that inspects medicine packets, which are packaged in the unit of a dose through an automatic medicine packing machine and discharged in a bundle from the medicine packing machine, to detect the number of tablets contained in the packets and whether or not the tablets are damaged.

Such a conventional medicine packet inspecting apparatus includes a transfer conveyer to transfer a medicine packet bundle discharged from the medicine packing machine to one side of the medicine packet inspecting apparatus, a tablet spreading unit to uniformly spread tablets within the medicine packets of the medicine packet bundle discharged through the transfer conveyer, an image reading unit to capture the upper surfaces of the medicine packets, in which the tablets are uniformly spread and to detect whether or not the medicine packets are defective through comparison of the number of the tablets and the colors and shapes of the tablets by comparing the captured images with information regarding a prescription and the tablets stored in a data storage unit, and a marking unit to mark a defective sign on medicine packets judged to be defective packets by the image reading unit.

In the above conventional medicine packet inspecting apparatus, since the medicine packet bundle input from the outside of a main body of the medicine packet inspecting apparatus is extended longitudinally to the outside of the medicine packet inspecting apparatus, it is difficult to collect the extended medicine packet bundle at a designated place. Further, continuous supply of the medicine packet bundle from the outside of the medicine packet inspecting apparatus to the inside of the medicine packet inspecting apparatus is inconvenient, and thereby an inspecting speed of the medicine packets by the medicine packet inspecting apparatus is remarkably reduced.

SUMMARY OF THE INVENTION

Therefore, the present invention has been made in view of the above problems, and it is an object of the present invention to provide a medicine packet inspecting apparatus, which allows medicine packets to be simply supplied within the medicine packet inspecting apparatus, improves an inspecting speed of the medicine packets, and increases convenience in use due to the simple supply of the medicine packets and the rapid inspecting speed of the medicine packets.

It is a further object of the present invention to provide a medicine packet inspecting apparatus, in which a bobbin is fixedly inserted into a rotary shaft with a simple structure such that rotation of the bobbin is stably and precisely carried out.

It is another object of the present invention to provide a medicine packet inspecting apparatus, in which a rotary shaft is rotated according to driving of a transfer conveyer such that a medicine packet bundle is stably and precisely unwound from the bobbin.

It is another object of the present invention to provide a medicine packet inspecting apparatus, in which a medicine packet bundle unwound from a bobbin is smoothly guided to a medicine packet spreading unit with a simple structure.

It is yet another object of the present invention to provide a medicine packet inspecting apparatus, in which a barcode printed on medicine packets is smoothly recognized while unwinding a medicine packet bundle from a bobbin.

In accordance with the present invention, the above and other objects can be accomplished by the provision of a medicine packet inspecting apparatus, which has a transfer conveyer installed on the upper surface of a main body to transfer medicine packets to one side of the main body, a tablet spreading unit installed on the upper surface of the transfer conveyer to uniformly spread tablets within the medicine packets, an image reading unit to capture the upper surfaces of the medicine packets with a camera and to judge whether or not the tablets are defective through comparison of the captured images with information regarding a prescription and the tablets stored in a data storage unit, and a making unit to mark a defective sign on medicine packets if the tablets within the medicine packets are judged to be defective, includes a bobbin support unit rotatably mounted on the front surface of the main body above the tablet spreading unit, a bobbin, on which a medicine packet bundle is wound, inserted into the bobbin support unit, and a bundle guide unit to guide the medicine packet bundle, unwound from the bobbin according to the rotation of the bobbin support unit, to the tablet spreading unit.

The bobbin support unit may include a rotary shaft penetrating the main body, a support tube mounted on the front surface of the main body so as to surround the rear end of the rotary shaft, and a pair of bearings mounted between the external surface of the rotary shaft and the internal surface of the support tube.

The bobbin support unit may further include a bobbin fixing unit installed at the front end of the rotary shaft to detachably fix the bobbin inserted into the front end of the rotary shaft.

The bobbin fixing unit may include a fixing clamp rotatably mounted at the front end of the rotary shaft and folded at a right angle to fix the bobbin, a support spring installed at the front end of the rotary shaft to elastically support the fixing clamp, a stopper horizontally movably installed in the rotary shaft corresponding to the rear end of the fixing clamp to stop the fixing clamp so as to rotate the fixing clamp at the right angle, an elastic spring provided within the rotary shaft to elastically support the stopper, and a hinge protrusion connected to the stopper and provided with the lower end hinged to the central part of the rotary shaft and the upper end folded by the bobbin inserted into the rotary shaft to release the fixed state of the fixing clamp by the stopper.

The bobbin fixing unit may further include a connection rod provided with the front end mounted on the rear end of the stopper and being horizontally movable along the inside of the rotary shaft, and a connection link provided with the front end hinged to the rear end of the connection rod and the rear end hinged to the hinge protrusion.

The hinge protrusion may be provided with an arc-shaped long hole formed through the central portion thereof, and the connection link may be provided with a hinge pin hinged to the rear end thereof, inserted into the arc-shaped long hole, and sliding along the arc-shaped long hole.

The bobbin fixing unit may further include a plate spring mounted between the front end of the hinge protrusion and the inside of the rotary shaft so as to elastically restore the hinge protrusion.

The fixing clamp may be provided with a round groove formed on the upper, lower, and rear surfaces thereof along the circumference of the rear end of the fixing clamp, and the stopper may be provided with a circular protrusion formed on the front end thereof such that the circular protrusion is inserted into the round groove.

The fixing clamp may be provided with a protrusion protruded from the upper and lower surfaces of the front end thereof, and the bobbin may be provided with an insertion groove formed on the front surface thereof such that the protrusion is inserted into the insertion groove.

The bobbin support unit may further include a motor driving unit installed within the main body to rotate the rotary shaft according to the operation of the transfer conveyer.

The bundle guide unit may include a guide plate mounted on the main body below the bobbin to guide the medicine packet bundle unwound from the bobbin to an area below the guide plate, and a guide rod rotatably mounted on the front surface of the main body between the lower end of the guide plate and the external surface of the tablet spreading unit to bend the medicine packet bundle, guided to the area below the guide plate, in the horizontal direction.

The medicine packet inspecting apparatus may further include a barcode scanner mounted on the front surface of the main body below the bobbin to scan a barcode printed on the external surfaces of the medicine packets transferred from the bobbin to the bundle guide unit.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, a preferred embodiment of the present invention will be described in detail with reference to the annexed drawings.

Figure 1:
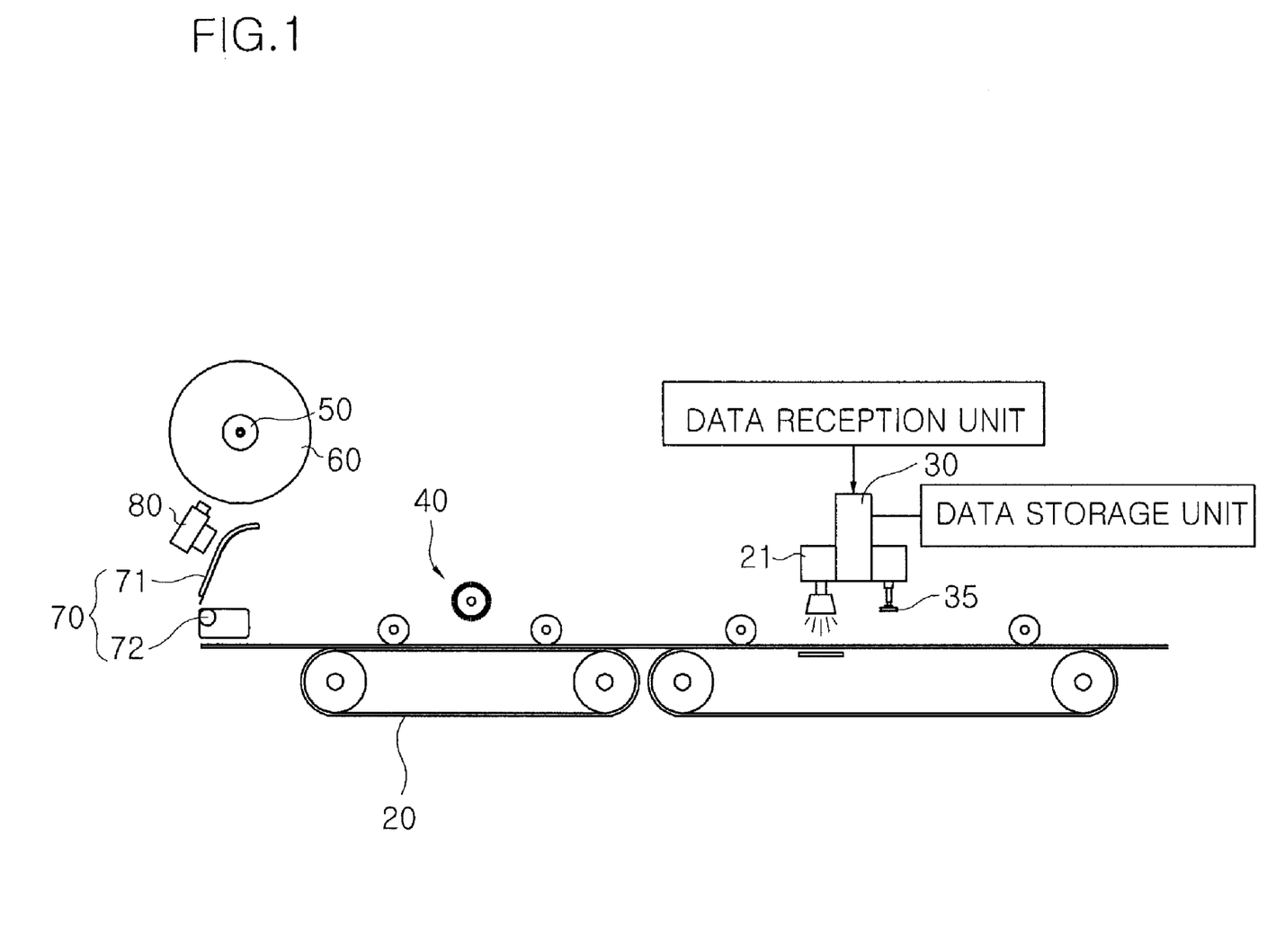
FIG. 1 is a schematic front view of a medicine packet inspecting apparatus in accordance with the present invention.
Figure 2:
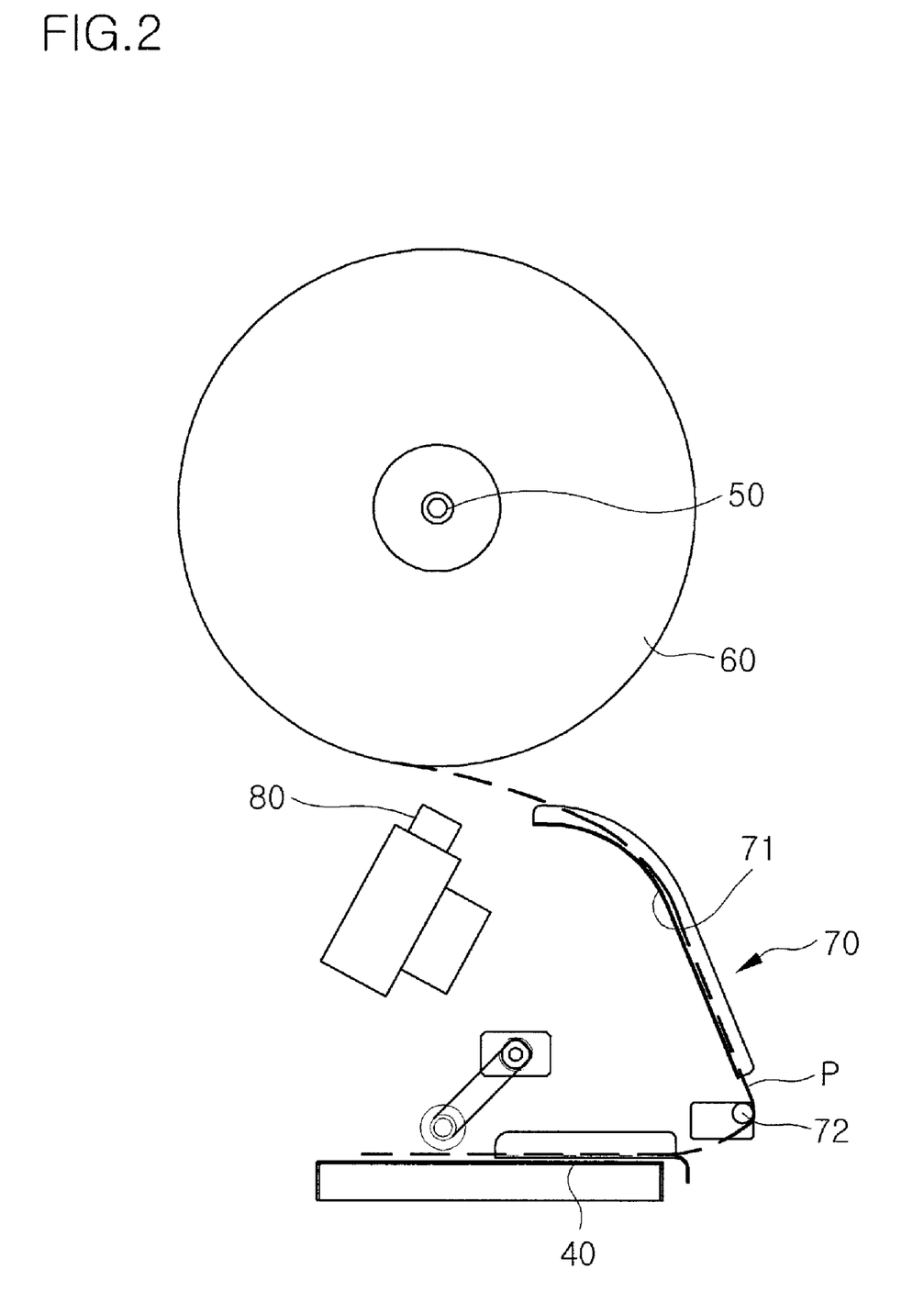
FIG. 2 is a schematic enlarged front view of an essential portion of the medicine packet inspecting apparatus in accordance with the present invention.

FIG. 1 is a schematic front view of a medicine packet inspecting apparatus in accordance with the present invention, and FIG. 2 is a schematic enlarged front view of an essential portion of the medicine packet inspecting apparatus in accordance with the present invention.

As shown in FIGS. 1 and 2, the medicine packet inspecting apparatus in accordance with the present invention includes a bobbin support unit 50, a bobbin 60 inserted into the bobbin support unit 50, and a bundle guide unit 70 to guide a medicine packet bundle unwound from the bobbin 60, which are installed on the upper surface of a main body 10 of the medicine packet inspecting apparatus. The medicine packet bundle from the bundle guide unit 70 is transferred to one side of a transfer conveyer 20. The medicine packet inspecting apparatus further includes a tablet spreading unit 40 to uniformly spread tablets within medicine packets on the upper surface of the transfer conveyer 20, an image reading unit 30 to capture the upper surfaces of the medicine packets transferred through the tablet spreading unit 40 with a camera 31 and to judge whether or not the number of the tablets and the colors and shapes of the tablets according to a prescription coincide with information regarding the tablets stored in a data storage unit through the captured images, and a marking unit 35 to mark a defective sign on medicine packets if the medicine packets are judged to be defective as the result of reading.

The bobbin support part 50 is rotatably mounted on the front surface of the main body 10 above the tablet spreading unit 40, and allows the bobbin 60, on which the medicine packet bundle is wound, to be inserted into the bobbin support part 50 and thus to be rotatably provided on the front surface of the main body 10.

The bobbin 60 is inserted into the bobbin support part 50 by a user under the condition that the medicine packet bundle is wound on the bobbin 60, thereby feeding the medicine packets to the inside of the inspecting apparatus. When all the medicine packets are unwound from the bobbin 60, the user separates the bobbin 60 from the bobbin support unit 50, rewinds a new medicine packet bundle, and then fixes the bobbin 60 to the bobbin support unit 50.

The bundle guide unit 70 serves to guide the medicine packet bundle, unwound from the bobbin 60 together with the rotation of the bobbin support unit 50, to the tablet spreading unit 40.

The above bundle guide unit 70 includes a guide plate 71 mounted on the front surface of the main body 10 below the bobbin 60, and a guide rod 72 rotatably mounted on the front surface of the main body 10 between the lower end of the guide plate 71 and the external surface of the tablet spreading unit 40.

The guide plate 71 serves to guide the medicine packet bundle unwound from the bobbin 60 to an area below the guide plate 71, and the guide rod 72 serves to bend the medicine packet bundle, guided to the area below the guide plate 71, in the horizontal direction and thus to change the position of the medicine packet bundle to the tablet spreading unit 40.

The inspecting apparatus further includes a barcode scanner 80 mounted on the front surface of the main body 10 below the bobbin 60. The barcode scanner 80 serves to scan a barcode printed on the external surfaces of the medicine packets transferred from the bobbin 60 to the bundle guide unit 70. The inspecting apparatus reads information of the medicine packets, on which inspection is performed, through the above barcode scanner 80, and transfers the read information to a control unit.

Figure 3:
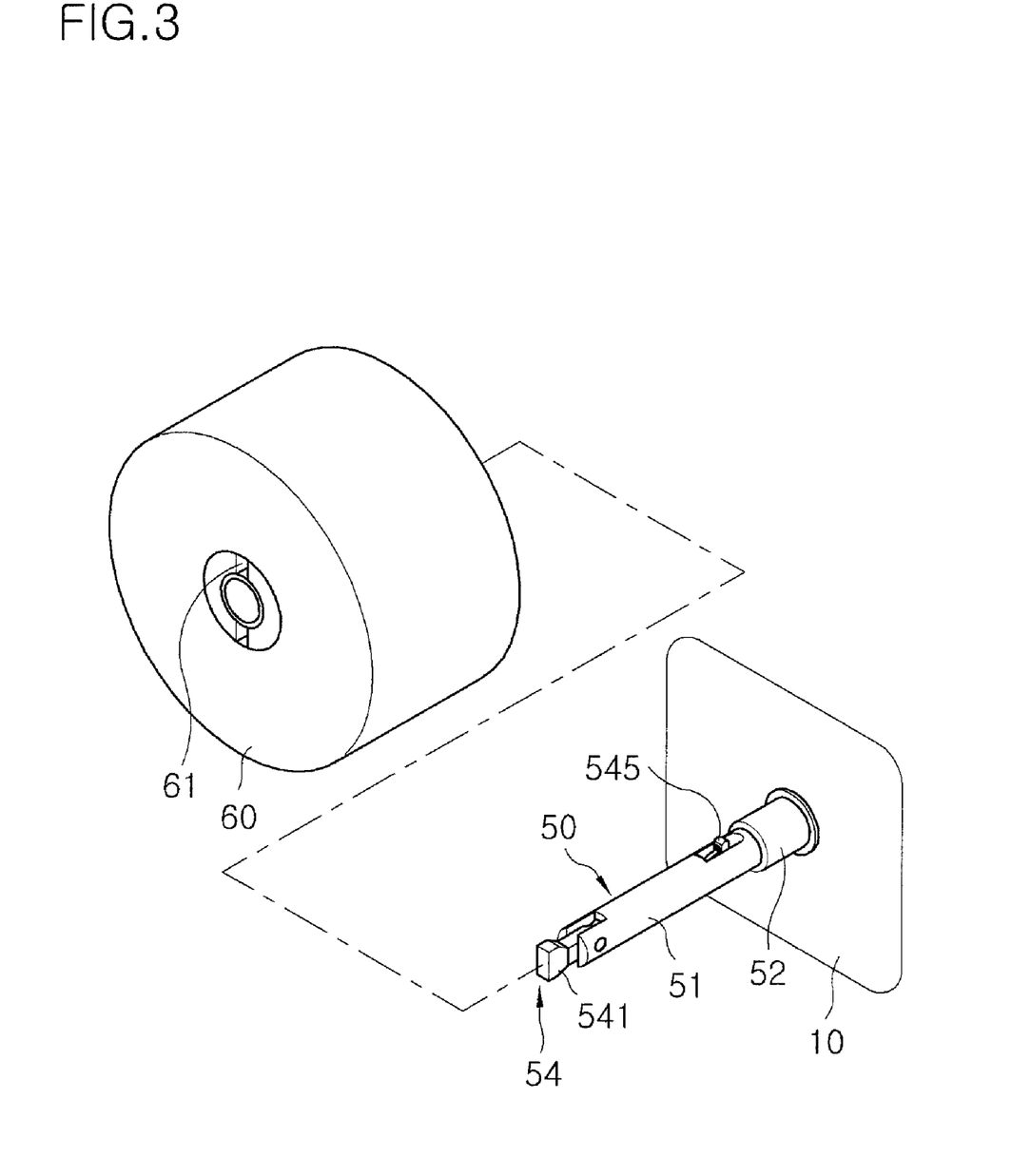
FIG. 3 is an exploded perspective view of the essential portion of the medicine packet inspecting apparatus in accordance with the present invention.
Figure 4:
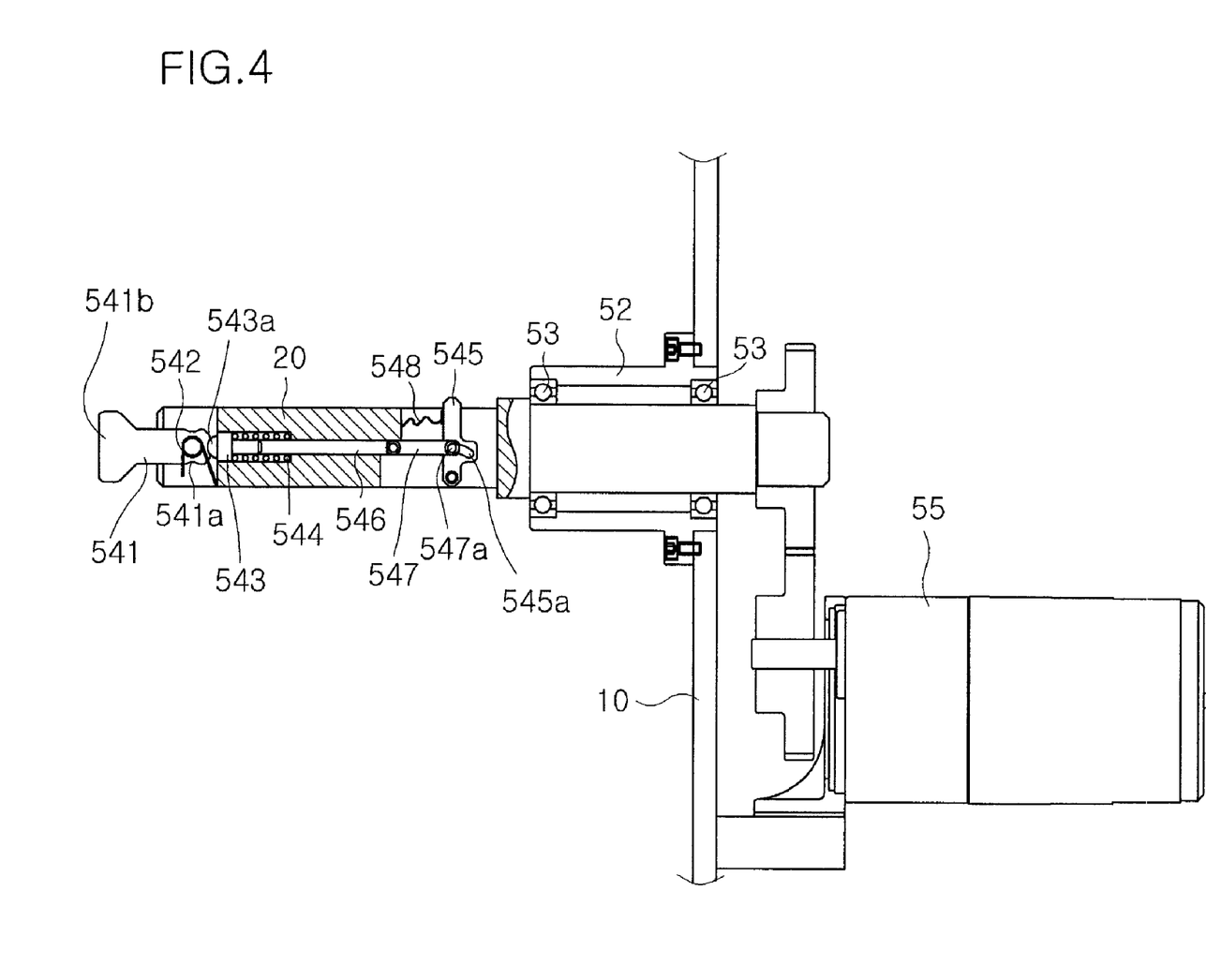
FIG. 4 is a longitudinal-sectional view of the essential portion of the medicine packet inspecting apparatus in accordance with the present invention.

FIG. 3 is an exploded perspective view of the essential portion of the medicine packet inspecting apparatus in accordance with the present invention, and FIG. 4 is a longitudinal-sectional view of the essential portion of the medicine packet inspecting apparatus in accordance with the present invention.

As shown in FIGS. 3 and 4, the bobbin support unit 50 includes a rotary shaft 51 penetrating the main body 10, a support tube 52 mounted on the front surface of the main body 10 so as to surround the rear end of the rotary shaft 51, and a pair of bearings 53 mounted between the external surface of the rotary shaft 51 and the internal surface of the support tube 52.

The rotary shaft 51, into which the bobbin 60 is inserted, serves to rotatably support the bobbin 60. The support tube 52 serves to support the bearing 53 so as to rotatably provide the rotary shaft 51 on the main body 10.

The bobbin support unit 50 further include a bobbin fixing unit 54 installed at the front end of the rotary shaft 51. The bobbin fixing unit 54 serves to detachably fix the bobbin 60 inserted into the front end of the rotary shaft 51.

The above bobbin fixing unit 54 includes a fixing clamp 541 rotatably mounted at the front end of the rotary shaft 51, a support spring 542 installed at the front end of the rotary shaft 51, a stopper 543 horizontally movably installed in the rotary shaft 51 corresponding to the rear end of the fixing clamp 541, an elastic spring 544 provided within the rotary shaft 51, and a hinge protrusion 545 connected to the stopper 543 and provided with the lower end hinged to the central part of the rotary shaft 51.

The fixing clamp 541 is folded at a right angle by releasing the fixed state of the fixing clamp 541 by the stopper 543 under the condition that the fixing clamp 541 is supported by the support spring 542, and thereby serves to fix the bobbin 60 or release the fixation of the bobbin 60. The support spring 542 serves to support a rotating part of the fixing clamp 541 and thus to apply an elastic restoring force to the fixing clamp 541.

The stopper 543 stops the fixing clamp 541 and thus rotates the fixing clamp 541 at the right angle. The elastic spring 544 serves to support the stopper 543 and thus to apply an elastic restoring force to the stopper 543. The upper end of the hinge protrusion 545 is folded by the bobbin 60 inserted into the rotary shaft 51, and thereby the hinge protrusion 545 serves to release the fixed state of the fixing clamp 541 by the stopper 543.

The bobbin support unit 54 further includes a connection rod 546 provided with the front end mounted on the rear end of the stopper 543 and being horizontally movable along the inside of the rotary shaft 51, and a connection link 547 provided with the front end hinged to the rear end of the connection rod 546 and the rear end hinged to the hinge protrusion 545.

The connection rod 546 is slidably provided within the rotary shaft 51, and thus serves to stably support a horizontal motion of the stopper 543. The connection link 547 serves to interconnect the hinge protrusion 545 and the connection rod 546 so as to change an angular motion of the hinge protrusion 545 into a horizontal motion of the connection rod 546.

The hinge protrusion 545 is provided with an arc-shaped long hole 545a, which is formed through the central portion thereof, and the connection link 547 is provided with a hinge pin 547a, which is hinged to the lower end thereof, is inserted into the arc-shaped long hole 545a, and slides along the arc-shaped long hole 545a.

The arc-shaped long hole 545a forms a clearance between the rear end of the connection link 547 and the hinge protrusion 545, and thus causes the stopper 543 to be pushed backward when the fixing clamp 541 is forcibly rotated. Further, the hinge pin 547a is rotatably inserted into the arc-shaped long hole 545a, and thus causes the connection link 547 to stably slide along the arc-shaped long hole 545a.

The bobbin fixing unit 54 further includes a plate spring 548 mounted between the front end of the hinge protrusion 545 and the inside of the rotary shaft 51. The plate spring 548 serves to apply an elastic restoring force to the hinge protrusion 545 so as to restore the hinge protrusion 545 to an erected state after the angular rotation of the hinge protrusion 545 is carried out by the push of the bobbin 60.

The fixing clamp 541 is provided with a round groove 541a formed on the upper, lower, and rear surfaces thereof along the circumference of the rear end of the fixing clamp 541, and the stopper 543 is provided with a circular protrusion 543a formed on the front end thereof. The fixing clamp 541 is fixed at an angle of 90 degrees by the stopper 543 by inserting the circular protrusion 543a into the round groove 541a. The circular protrusion 543a is inserted into the round groove 541a and thus serves to fix the fixing clamp 541, or is separated from the round groove 541a and thus serves to release the fixed state of the fixing clamp 541.

The fixing clamp 541 is further provided with a protrusion 541b protruded from the upper and lower surfaces of the front end thereof, and the bobbin 60 is provided with an insertion groove 61 formed on the front surface thereof. The protrusion 541a is inserted into or separated from the insertion groove 61 of the bobbin 60 together with the folding of the fixing clamp 541, and thus serves to fix the bobbin 60 to the rotary shaft 51 or release the fixation of the bobbin 60 to the rotary shaft 51.

The bobbin support unit 50 further includes a motor driving unit 55 installed within the main body 10 to rotate the rotary shaft 51 according to the operation of the transfer conveyer 20. The motor driving unit 55 is driven in connection with the operation of the transfer conveyer 20 and thus rotates the bobbin 60 together with the rotary shaft 51, thereby allowing the medicine packet bundle wound on the bobbin 60 to be stably unwound from the bobbin 60.

Figure 5:
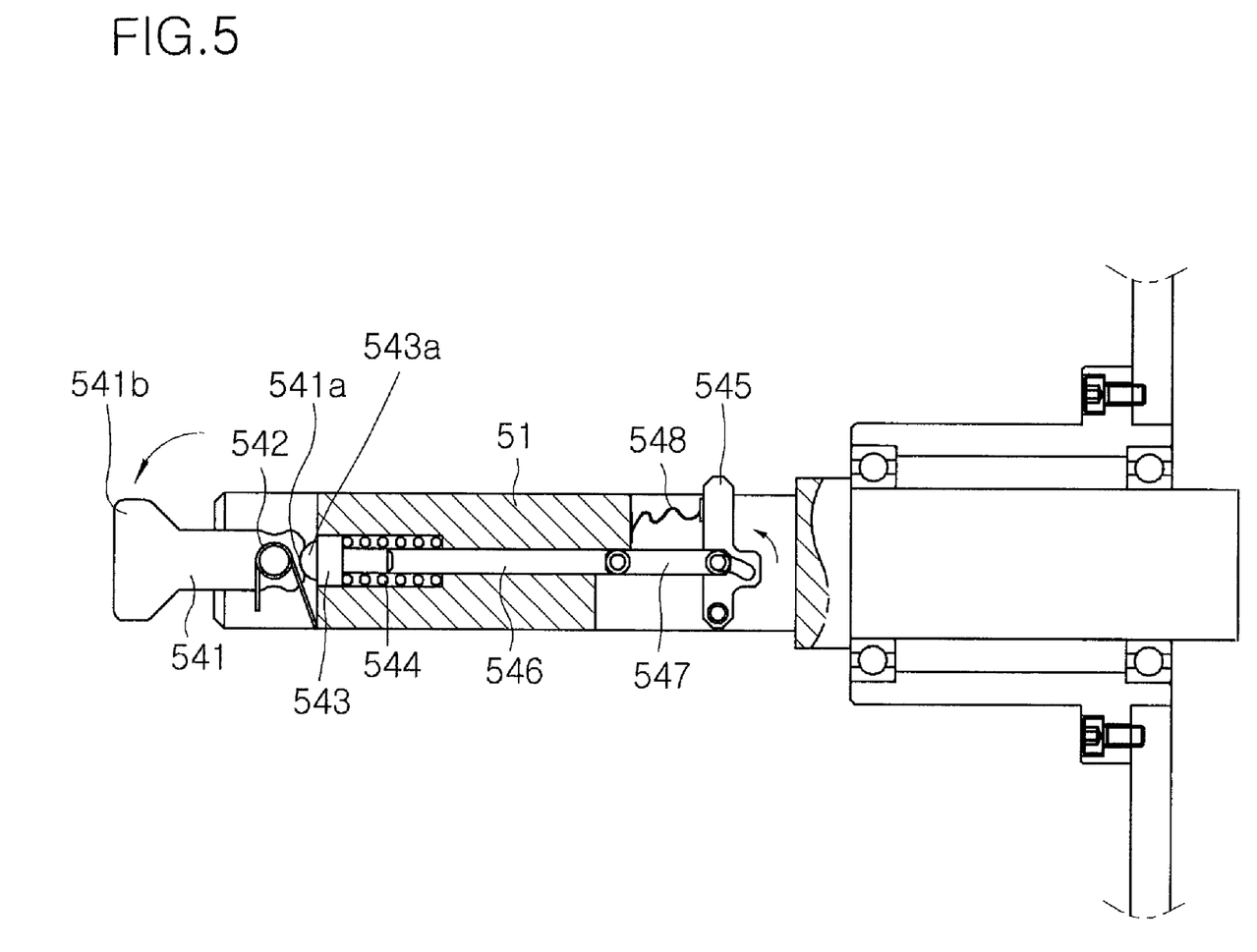
FIG. 5 is a longitudinal-sectional view of the essential portion of the medicine packet inspecting apparatus in accordance with the present invention, illustrating a state before a bobbin is fixed.
Figure 6:
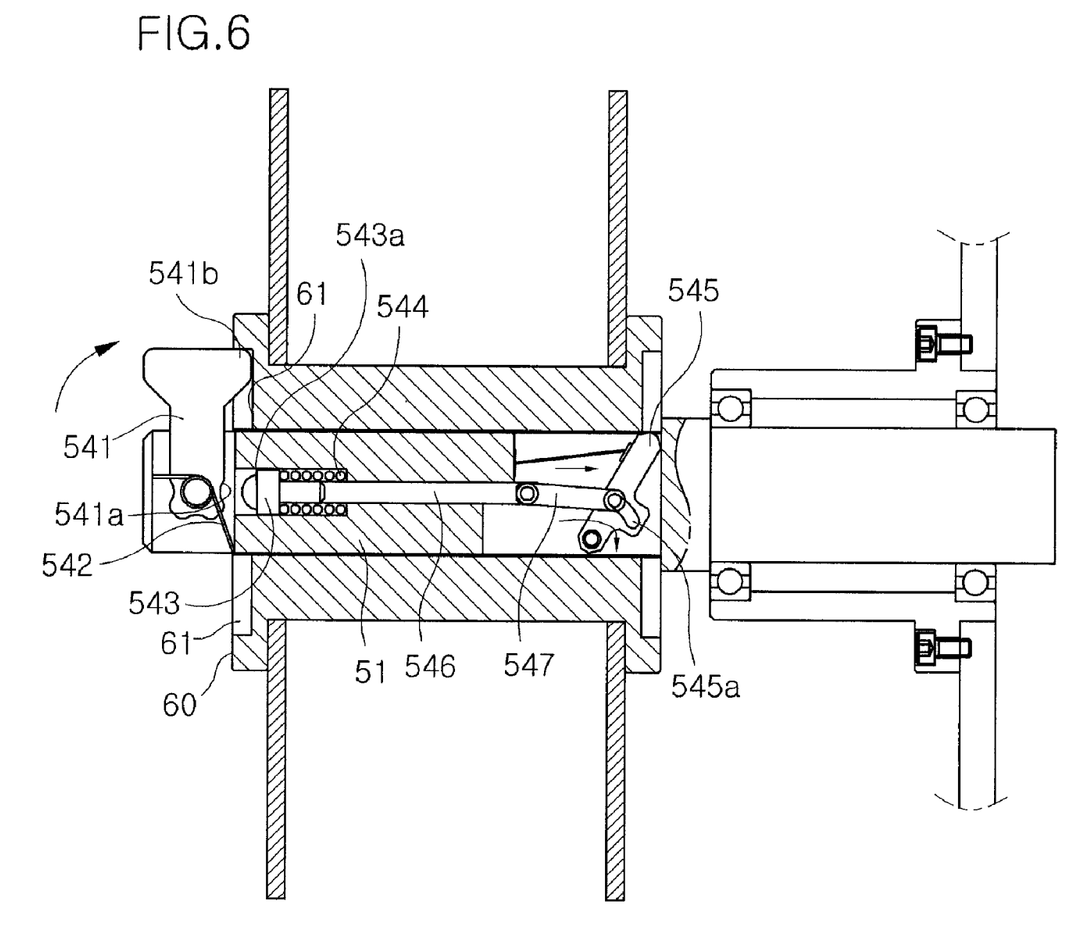
FIG. 6 is a longitudinal-sectional view of the essential portion of the medicine packet inspecting apparatus in accordance with the present invention, illustrating a state after the bobbin is fixed.

FIG. 5 is a longitudinal-sectional view of the essential portion of the medicine packet inspecting apparatus in accordance with the present invention, illustrating a state before the bobbin is fixed, and FIG. 6 is a longitudinal-sectional view of the essential portion of the medicine packet inspecting apparatus in accordance with the present invention, illustrating a state after the bobbin is fixed.

As shown in FIGS. 5 and 6, the fixing clamp 541 maintains a horizontal state at the front end of the rotary shaft 51, before the bobbin 60 is fixed. At this time, the hinge protrusion 545 installed on the rotary shaft 51 is restored from a forward folded state to an erected state by the plate spring 548, and then maintains the erected state.

When the fixing clamp 541 is folded to the front end of the rotary shaft 51, the support spring 542 is pressurized, and the stopper 543 supporting and fixing the fixing clamp 541 is also supported by the elastic spring 544.

When a user inserts the bobbin 60 into the rotary shaft 51 under the above state, the bobbin 60 is inserted into the rotary shaft 51 and causes the hinge protrusion 545 to be folded backward, and thereby the connection link 547 connected to the hinge protrusion 545 is drawn backward.

As the connection link 547 is drawn backward, the connection rod 546 connected to the connection link 547 slides backward within the rotary shaft 51. The elastic spring 544 is pressurized according to the sliding of the connection rod 546, and the stopper 543 is pushed backward and thus the circular protrusion 543a is separated from the round groove 541a. Thereby, the fixation of the fixing clamp 541 by the stopper 543 is released.

At this time, the fixing clamp 541 is folded upward at the right angle by the release of force from the pressurized support spring 542, and assumes the erected state. The bobbin 60 is fixed by the fixing clamp 541 by inserting the protrusion 541b of the fixing clamp 541 to the insertion groove 61 of the bobbin 60 under the above state. Further, the elastic spring 544 is pressurized by the backward movement of the stopper 543.

In order to separate the bobbin 60 from the rotary shaft 51, when the user takes the bobbin 60 out of the rotary shaft 51, the fixing clamp 541 is forcibly rotated, and assumes the horizontal state. Then, the fixation of the bobbin 60 by the fixing clamp 541 is released, and thus the bobbin 60 is separated from the rotary shaft 51.

At this time, the push of the hinge protrusion 545 by the bobbin 60 is released and thus the hinge protrusion 545 is erected by the plate spring 548, and the backward push of the connection rod 546 connected to the connection link 547 is released and thus the stopper 543 moves forward together with the connection link 547 and the connection rod 546 by the restoring force of the elastic spring 544. As the stopper 543 moves forward in this manner, the circular protrusion 543a is inserted into the round groove 541a of the fixing clamp 541 in the horizontal state, and the fixing clamp 541 is fixed under the condition that the fixing clamp 541 is pressurized by the support spring 542.

When the fixing clamp 541 is forcibly rotated, the stopper 543 is pushed slightly backward. The backward movement of the stopper 543 is carried out by the clearance between the hinge protrusion 545 and the connection link 547 formed by the arc-shaped long hole 545a.

As apparent from the above description, the present invention provides a medicine packet inspecting apparatus, which allows medicine packets to be simply supplied within the medicine packet inspecting apparatus, remarkably improves an inspecting speed of the medicine packets, and increases convenience in use due to the simple supply of the medicine packets and the rapid inspecting speed of the medicine packets.

The medicine packet inspecting apparatus has a simple structure, is easily manufactured and installed, and allows a bobbin to be fixedly inserted into a rotary shaft such that rotation of the bobbin is stably and precisely carried out.

The medicine packet inspecting, apparatus allows the rotary shaft to be rotated according to driving of a transfer conveyer such that a medicine packet bundle is stably and precisely unwound from the bobbin, thereby stably and precisely carrying out supply of medicine packets for inspection.

The medicine packet inspecting apparatus allows the medicine packet bundle unwound from the bobbin to be smoothly guided to a medicine packet spreading unit, thereby improving stability in operation.

The medicine packet inspecting apparatus causes a barcode printed on the medicine packets to be smoothly recognized while unwinding the medicine packet bundle from the bobbin, thereby simply obtaining information regarding the medicine packets.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A medicine packet inspecting apparatus, which has
a transfer conveyer installed on the upper surface of a main body to transfer medicine packets to one side of the main body,
a tablet spreading unit installed on the upper surface of the transfer conveyer to uniformly spread tablets within the medicine packets,
an image reading unit to capture the upper surfaces of the medicine packets with a camera and to judge whether or not the tablets are defective through comparison of the captured images with information regarding a prescription and the tablets stored in a data storage unit, and
a making unit to mark a defective sign on medicine packets if the tablets within the medicine packets are judged to be defective, comprising:
a bobbin support unit rotatably mounted on the front surface of the main body above the tablet spreading unit;
a bobbin, on which a medicine packet bundle is wound, inserted into the bobbin support unit; and
a bundle guide unit to guide the medicine packet bundle, unwound from the bobbin according to the rotation of the bobbin support unit, to the tablet spreading unit,
wherein the bobbin support unit includes:
a rotary shaft penetrating the main body;
a support tube mounted on the front surface of the main body so as to surround the rear end of the rotary shaft; and
a pair of bearings mounted between the external surface of the rotary shaft and the internal surface of the support tube,
wherein the bobbin support unit further includes a bobbin fixing unit installed at the front end of the rotary shaft to detachably fix the bobbin inserted into the front end of the rotary shaft,
wherein the bobbin fixing unit includes:
a fixing clamp rotatably mounted at the front end of the rotary shaft and folded at a right angle to fix the bobbin;
a support spring installed at the front end of the rotary shaft to elastically support the fixing clamp;
a stopper horizontally movably installed in the rotary shaft corresponding to the rear end of the fixing clamp to stop the fixing clamp so as to rotate the fixing clamp at the right angle;
an elastic spring provided within the rotary shaft to elastically support the stopper; and
a hinge protrusion connected to the stopper and provided with the lower end hinged to the central part of the rotary shaft and the upper end folded by the bobbin inserted into the rotary shaft to release the fixed state of the fixing clamp by the stopper,
wherein the bobbin fixing unit further includes:
a connection rod provided with the front end mounted on the rear end of the stopper and being horizontally movable along the inside of the rotary shaft; and
a connection link provided with the front end hinged to the rear end of the connection rod and the rear end hinged to the hinge protrusion,
wherein:
the hinge protrusion is provided with an arc-shaped long hole formed through the central portion thereof; and
the connection link is provided with a hinge pin hinged to the rear end thereof, inserted into the arc-shaped long hole, and sliding along the arc-shaped long hole,
wherein the bobbin fixing unit further includes:
a plate spring mounted between the front end of the hinge protrusion and the inside of the rotary shaft so as to elastically restore the hinge protrusion,
wherein:
the fixing clamp is provided with a round groove formed on the upper, lower, and rear surfaces thereof along the circumference of the rear end of the fixing clamp; and
the stopper is provided with a circular protrusion formed on the front end thereof such that the circular protrusion is inserted into the round groove, wherein:

the fixing clamp is provided with a protrusion protruded from the upper and lower surfaces of the front end thereof; and the bobbin is provided with an insertion groove formed on the front surface thereof such that the protrusion is inserted into the insertion groove.

2. The medicine packet inspecting apparatus according to claim 1, wherein the bobbin support unit further includes a motor driving unit installed within the main body to rotate the rotary shaft according to the operation of the transfer conveyer.

3. The medicine packet inspecting apparatus according to claim 1, wherein the bundle guide unit includes:

a guide plate mounted on the main body below the bobbin to guide the medicine packet bundle unwound from the bobbin to an area below the guide plate; and a guide rod rotatably mounted on the front surface of the main body between the lower end of the guide plate and the external surface of the tablet spreading unit to bend the medicine packet bundle, guided to the area below the guide plate, in the horizontal direction.

4. The medicine packet inspecting apparatus according to claim 1, further comprising a barcode scanner mounted on the front surface of the main body below the bobbin to scan a barcode printed on the external surfaces of the medicine packets transferred from the bobbin to the bundle guide unit.

* * * * *